United States Patent [19]

Oda et al.

[11] Patent Number: 4,472,578
[45] Date of Patent: Sep. 18, 1984

[54] BENZO[A]PHENAZINE ANTIMICROBIALS

[75] Inventors: Noriichi Oda, Okazaki; Kazuhiro Kobayashi, Konan; Isoo Ito, Mie, all of Japan

[73] Assignee: Taisho Pharmaceutical Co., Ltd., Japan

[21] Appl. No.: 478,010

[22] Filed: Mar. 23, 1983

[30] Foreign Application Priority Data

Sep. 29, 1982 [JP] Japan ................................ 57-170099

[51] Int. Cl.³ .................. C07D 241/46; C07D 413/14; C07D 413/12; C07D 413/06
[52] U.S. Cl. ...................................... 544/347; 544/80; 544/115; 424/248.54; 424/248.55
[58] Field of Search .......................... 544/347, 80, 115

[56] References Cited

U.S. PATENT DOCUMENTS 4,316,959 2/1982 Michel et al. ........................ 435/122

*Primary Examiner*—Mark L. Berch
*Attorney, Agent, or Firm*—Kenway & Jenney

[57] ABSTRACT

There have been prepared novel benzo[a]phenazine derivatives of the formula

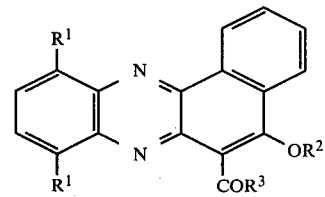

wherein $R^1$ is hydrogen or methoxy, $R^2$ is hydrogen, methyl, acetyl, haloacetyl or substituted aminoalkyl, and $R^3$ is ethoxy or substituted amino. These compounds are useful as antimicrobiological agents.

5 Claims, No Drawings

BENZO[A]PHENAZINE ANTIMICROBIALS

The present invention relates to novel benzo[a]phenazine derivatives useful as anti-microbiological agents.

Although phenazine compounds having anti-bacterial activity, have been known in the prior art the compounds of the present invention contain four condensed rings unlike the previously known antibacterial phenazine compounds, and have high anti-microbiological activity against fungi and bacteria with extremely lower toxicity than the previously known phenazine compounds.

The compounds of the present invention are represented by the formula

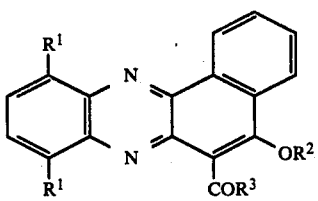

I wherein $R^1$ is hydrogen or methoxy,
$R^2$ is hydrogen, methyl, acetyl, haloacetyl or substituted aminoalkyl of the formula

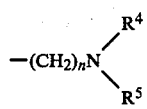

II wherein $R^4$ and $R^5$ are alkyl having 2 or 3 carbon atoms, or $R^4$ and $R^5$ together with the nitrogen atom to which they are attached form morpholino or piperidino, and n is 2 or 3, and $R^3$ is ethoxy or substituted amino of the formula

III wherein $R^6$ is hydrogen and $R^7$ is alkyl which has 2 or 3 carbon atoms and is substituted with halogen, hydroxy, acetoxy or sec-amino, and $R^6$ and $R^7$ together with the nitrogen atom to which they are attached form morpholino.

The term "sec-amino" in the specification means dimethylamino, diethylamino, morpholino or piperidino, and the terms "halo" and "halogen" mean fluorine, chlorine, bromine or iodine.

Preferred compounds of formula I are those wherein $R^1$ is hydrogen or methoxy, $R^2$ is hydrogen and $R^3$ is dimethylaminoethylamino or dimethylaminopropylamino.

The compounds of the invention may be prepared by the following methods.

(1) Ethyl 1,4-dihydroxy 1,4-dioxo-3-methoxy-2-naphtoate is reacted with a compound of the formula

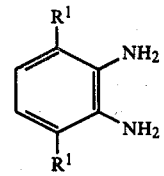

IV wherein $R^1$ is as defined above, in the presence of an organic solvent such as ethanol or dimethylformamide to give a compound of the formula

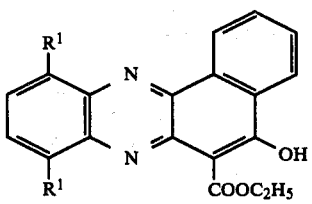

Ia wherein $R^1$ is as defined above.

(2) The compound of formula I wherein $R^2$ is hydrogen and $R^3$ is other than ethoxy can be prepared by reacting the compound of formula Ia with a compound of the formula

V wherein $R^6$ and $R^7$ are as defined above, in the presence of a base such as sodium carbonate or sodium ethoxide in an organic solvent such as benzene, ethanol or toluene.

(3) The compound of formula I wherein $R^2$ is other than hydrogen can be prepared from the compound of formula I wherein $R^2$ is hydrogen, which is obtained according to synthesis (1) or (2) above. Specifically, the compound of formula I wherein $R^2$ is methyl can be prepared by reacting the compound of formula I wherein $R^2$ is hydrogen with a methylating agent such as diazomethane in the presence of an organic solvent such as diethyl ether or methanol.

The compound of formula I wherein $R^2$ is sec-aminoalkyl wherein the alkyl moiety contains 2 or 3 carbon atoms can be prepared by reacting the compound of formula I wherein $R^2$ is hydrogen with a compound of the formula

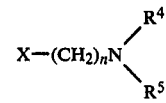

VI wherein $R^4$, $R^5$ and n are as defined above and X is halogen, in the presence of a base such as sodium hydride or potassium hydride in an aprotic solvent such as benzene, toluene or xylene.

The compound of formula I wherein $R^2$ is acetyl or haloacetyl can be prepared by the reaction of the compound of formula I wherein $R^2$ is hydrogen with a acetylating agent such as acetyl chloride or haloacetyl chloride in the presence of a base such as triethylamine in an aprotic solvent such as benzene or toluene.

(4) Alternatively, the compound of formula I wherein $R^2$ is hydrogen and $R^3$ is haloalkylamino can be prepared by the reaction of the compound of formula I wherein $R^2$ is hydrogen and $R^3$ is hydroxyalkylamino, which is obtained by synthesis (2), with a halogenating agent such as thionyl halide in the presence of a base such as triethylamine.

The compound of formula I wherein $R^2$ is hydrogen and $R^3$ is acetoxyalkylamino can be prepared by the reaction of the compound of formula I wherein $R^2$ is hydrogen and $R^3$ is hydroxyalkylamino, which is obtained by synthesis (2), with an acetylating agent such as acetyl halide.

The compound of formula I wherein $R^2$ is hydrogen and $R^3$ is sec-aminoalkylamino can be also prepared by a reaction of the compound of formula I wherein $R^2$ is hydrogen and $R^3$ is haloalkylamino, which is obtained as above, with dimethylamine, diethylamine, morpholine or piperidine in an organic solvent such as ethanol or dimethylformamide in the presence or absence of a base such as sodium carbonate or potassium carbonate.

The compound of formula I wherein $R^2$ is hydrogen and $R^3$ is morpholino can be also prepared by a reaction of the compound of formula I wherein $R^2$ is other than hydrogen and $R^3$ is ethoxy, which is obtained in synthesis (3), with morpholine in an organic solvent such as pyridine.

The compounds of formulae II, III, IV, V and VI can be conveniently prepared by conventional methods.

The compounds of the present invention have excellent anti-microbiological activity against fungi and bacteria in mammals, show extremely low toxicity, and therefore, are useful as anti-microbiological agents. The compounds of formula I may be administered orally in conventional dosage form such as tablets, capsules, powders, granules or syrups according to conventional pharmaceutical practices.

The effective dosage of the compound of the present invention depends on the age, weight or response of the patient. Generally, however, the daily dosage in adults may range from 600–1000 mg in single or divided doses.

The compounds of the present invention have extremely low toxicity. The acute toxicities ($LD_{50}$) in mice of the present compounds administered orally and intraperitoneally are in the range of 2500–3000 mg/kg and 2500–3500 mg/kg, respectively. In contrast the $LD_{50}$ in mice of 6-[1-[(2-hydroxy-6-methylbenzyl)oxy]ethyl]-1-phenazinecarboxylic acid (described in U.S. Pat. No. 4,316,959) administered intraperitoneally is 125 mg/kg.

EXPERIMENT

Two varieties of microorganisms, *Staphylococcus aureus* 209P and *Trichophyton interdigitale* TISD were employed as test microorganisms in an MHA medium (product of Eiken) for the former microorganism and in a medium containing 2% by weight of sorbitol, 0.15% by weight of L-asparagine, 0.67% by weight of yeast nitrogen base (product of Difco) and 1.5% by weight of agar powders for the latter microorganism.

Each test compound was dissolved in chloroform to a concentration of 500 μg/ml, and 50 μg of the solution was soaked in paper disk. The paper disk was dried and placed on test microorganism plate. The plate was incubated at 37° C. overnight for the former microorganism and at 30° C. for 2 days for the latter microorganism. The antimicrobiological activity of the test compounds was elevated by measuring diameter (mm) of controlled circles.

The results are given in Table 1.

TABLE 1

| | Antimicrobiological activities (diameter of the controlled circle/mm) | |
|---|---|---|
| Compound | *Staphylococcus aureus* 209P | *Trichophyton interdigitale* TISD |
| A | 11.9 | 14.6 |
| B | — | 12.5 |
| C | — | 19.0 |
| D | 10.9 | 10.5 | note
Compound names corresponding to Symbols A–D are as follows:
A: The compound of formula I wherein $R^1$ is hydrogen, $R^2$ is N,N—dimethylaminopropyl and $R^3$ is ethoxy.
B: The compound of formula I wherein $R^1$ is hydrogen, $R^2$ is N,N—diethylaminoethyl and $R^3$ is ethoxy.
C: The compound of formula I wherein $R^1$ is hydrogen, $R^2$ is morpholinoethyl and $R^3$ is ethoxy.
D: The compound of formula I wherein $R^1$ and $R^2$ are hydrogen and $R^3$ is N,N—dimethylaminoethylamino.

Syntheses of compounds of the present invention are illustrated by the following examples.

EXAMPLE 1

A mixture of 2.63 g of ethyl 1,4-dihydro-1,4-dioxo-3-methoxy-2-naphthoate and 1.3 g of o-phenylenediamine in 50 ml of ethanol was heated at reflux for an hour. After cooling, the precipitated solid was collected by filtration and recrystallized from ethanol to give 2.972 g (93.5% yield) of ethyl 5-hydroxybenzo[a]phenazine-6-carboxylate as yellow needles, m.p. 126°–127° C., Anal. CAlcd. (%) for $C_{19}H_{14}N_2O_3$: C, 71.69; H, 4.43; N, 8.80; Found: C, 71.81; H, 4.21; N, 8.90

EXAMPLE 2

In 50 ml of hot ethanol was dissolved 1.68 g of 3,6-dimethoxy-o-phenylenediamine. To this solution was gradually added 2.6 g of ethyl 1,4-dihydro-1,4-dioxo-3-methoxy-2-naphthoate under heating with stirring, and the mixture was refluxed for a further 2 hours. The reaction mixture was cooled and the precipitated solid was collected by filtration and recrystallized from benzene to give 3.50 g (92.6% yield) of ethyl 5-hydroxy-8,11-dimethoxybenzo[a]-phenazine-6-carboxylate as red needles, m.p. 290° C. (decomp.), Anal. Calcd.: (%) for $C_{21}H_{18}N_2O_5$; C, 66.66; H, 4.80; N, 7.40; Found: C, 66.46; H, 4.56; N, 7.53

EXAMPLE 3

An excess amount of diazomethane ethereal solution was added to a suspension of 640 mg of ethyl 5-hydroxybenzo[a]-phenazine-6-carboxylate in 8 ml of methanol and the mixture was left to stand overnight. The solvent was evaporated off under reduced pressure and the residual powder was recrystallized from ethanol to give 626 mg (91.5% yield) of ethyl 5-methoxybenzo[a]-phenazine-6-carboxylate as orange prisms, m.p. 155°–157° C., Anal. Calcd. (%) for $C_{20}H_{16}N_2O_3$: C, 72.28; H, 4.85; N, 8.43; Found: C, 72.41; H, 4.66; N, 8.18

EXAMPLE 4

A mixture of 640 mg ethyl 5-hydroxybenzo[a]phenazine-6-carboxylate, 6 ml of acetic anhydride and two drops of pyridine was stirred overnight and poured into water. The precipitated solid was collected by filtration and recrystallized from ethanol to give 600 mg (91.1% yield) of ethyl 5-acetoxybenzo[a]phenazine-6-carboxylate as orange needles, m.p. 195°–196° C., Anal. Calcd. (%) for $C_{21}H_{16}N_2O_4$: C, 69.99; H, 4.48; N, 7.77; Found: C, 70.12; H, 4.45; N, 7.63

EXAMPLE 5

A mixture of 635 mg of ethyl 5-hydroxybenzo[a]-phenazine-6-carboxylate, 283 mg of chloroacetyl and 1 mg of 4-dimethylaminopyridine (DMAP) in dry chloroform was heated at reflux for 10 hours. After cooling, the solvent was concentrated under reduced pressure. A small amount of benzene was added to the residue for crystallization to give 463 mg (58.6% yield) of ethyl 5-chloroacetoxybenzo[a]-phenazine-6-carboxylate as orange prisms, m.p. 208°–209° C., Anal. Calcd. (%) for $C_{21}H_{15}N_2O_4Cl$: C, 63.89; H, 3.83; N, 7.10; Found: C, 63.78; H, 3.70; N, 6.86

EXAMPLE 6

(1) In 30 ml of dry benzene was dissolved 636 mg of ethyl 5-hydroxybenzo[a]phenazine-6-carboxylate, and 29 mg (1.2 eq.) of sodium hydride were then added. The mixture was heated at reflux for 3 hours.

To the reaction mixture was added 1.0 g of dry 3-dimethyl-aminopropyl chloride prepared from 3-dimethyl-aminopropyl chloride. The mixture was heated at reflux for 24 hours.

The reaction mixture was cooled and poured into water, and the mixture was stirred. The benzene layer was separated, and the remaining aqueous phase was extracted several times with chloroform. The combined organic solution was dried and evaporated to dryness. The residue was recrystallized from petroleum ether to afford 508 mg (63% yield) of ethyl 5-γ-dimethylaminopropyloxybenzo[a]phenazine-6-carboxylate as orange prisms, m.p. 85°–87° C., Anal. Calcd. (%) for $C_{24}H_{25}N_3O_3$: C, 71.44; H, 6.25; N, 10.41; Found: C, 71.37; H, 6.23; N, 10.29

(2) The following compounds were obtained in accordance with a procedure similar to that of item (1) using the respective secondary aminoalkyl chloride corresponding to each product.

Ethyl 5-β-diethylaminoethyloxybenzo[a]phenazine-6-carboxylate, yellow prisms, 25% yield, m.p. 57°–59° C., Anal. Calcd. (%) for $C_{25}H_{27}N_3O_3$: C, 71.92; H, 6.52; N, 10.06; Found: C, 71.82; H, 6.33; N, 10.13

Ethyl 5-β-morpholinoethyloxybenzo[a]phenazine-6-carboxylate, orange prisms, 32% yield, m.p. 107°–109° C., Anal. Calcd. (%) for $C_{25}H_{25}N_3O_4$: C, 69.59; H, 5.84; N, 9.74; Found: C, 69.61; H, 5.75; N, 9.69

Ethyl 5-β-piperidinoethyloxybenzo[a]phenazine-6-carboxylate, orange prisms, 40% yield, m.p. 97°–98° C., Anal. Calcd. (%) for $C_{26}H_{27}N_3O_3$: C, 72.57; H, 6.51; N, 9.77; Found: C, 72.79; H, 6.29; N, 9.69

(3) The following compounds were obtained in accordance with a procedure similar to that of item (1) using ethyl 5-hydroxy-8,11-dimethoxybenzo[a]phenazine-6-carboxylate as the starting material, of dry benzene and dimethylformamide as the solvent, and the respective secondary aminoalkyl chloride corresponding to each product.

Ethyl 5-γ-dimethylaminopropyloxy-8,11-dimethoxybenzo-[a]-6-carboxylate, yellow amorphous powder, 78% yield, m.p. 129°–130° C., Anal Calcd. (%) for $C_{26}H_{29}N_3O_5$: C, 67.38; H, 6.31; N, 9.07, Found: C, 67.08; H, 6.03; N, 9.06

Ethyl 5-β-diethylaminoethyloxy-8,11-diemthoxybenzo[a]-phenazine-6-carboxylate, orange amorphous powder, 87% yield, m.p. 111°–113° C., Anal. Calcd. (%) for $C_{27}H_{31}N_3O_5$: C, 67.90; H, 6.54; N, 8.80; Found: C, 68.05; H, 6.44; N, 8.63

Ethyl 5-β-morphlinoethyloxy-8,11-dimethoxybenzo[a]-phenazine-6-carboxylate, orange prisms, 89% yield, m.p. 153°–154° C., Anal. Calcd. (%) for $C_{27}H_{29}N_3O_6$: C, 67.90; H, 6.54; N, 8.80; Found: C, 68.05; H, 6.44; N, 8.80

Ethyl 5-β-piperidinoethyloxy-8,11-dimethoxybenzo[a]-phenazine-6-carboxylate, orange amorphous powder, 85% yield, m.p. 118°–121° C., Anal. Calcd. (%) for $C_{28}H_{31}N_3O_5$: C, 68.69; H, 6.38; N, 8.58; Found: C, 68.58; H, 6.56; N, 8.53

EXAMPLE 7

In 4 ml of pyridine were dissolved 200 mg of ethyl 5-chloroacetoxybenzo[a]phenazine-6-carboxylate and 220 mg of morpholine, and the solution was heated at 80°–100° C., for 3 hours. The reaction mixture was evaporated to dryness under reduced pressure. Water was added, and the precipitated solid was collected to give 130 mg (71.1% yield) of 5-hydroxy-6-morpholinocarbonylbenzo[a]phenazine as red amorphous powder, m.p. 223°–225° C., Anal. Calcd. (%) for $C_{21}H_{17}N_2O_3$: C, 70.18; H, 4.77; N, 11.69; Found: C, 69.94; H, 4.86; N, 11.86

EXAMPLE 8

A mixture of 1.59 g of ethyl 5-hydroxybenzo[a]-phenazine-6-carboxylate and 10 ml of ethanolamine was heated at 150°–160° C. with stirring for an hour.

The reaction mixture was added to ethanol for crystallization to give 1.619 g (96.9% yield) of the desired product, 5-hydroxy-N-β-hydroxyethylbenzo[a]phenazine-6-carboxyamide as yellow needles, m.p. 273°–274° C., Anal. Calcd. (%) for $C_{19}H_{15}N_3O_3$: C, 68.46; H, 4.54; N, 12.60; Found: C, 68.47; H, 4.27; N, 12.55

EXAMPLE 9

145 mg of 5-hydroxy-N-β-hydroxyethylbenzo[a]-phenazine-6-carboxyamide was treated with 2 ml of acetic anhydride and two drops of pyridine at room temperature overnight.

The reaction mixture was poured into ice-water. The precipitated solid was collected by filtration and recrystallized from ethanol to give 167 mg (94.4% yield) of 5-hydroxy-N-β-acetoxyethylbenzo[a]phenazine-6-carboxyamide as yellow needles, m.p. 138°–139° C., Anal. Calcd. (%) for $C_{21}H_{17}N_3O_4$: C, 67.19; H, 4.57; N, 11.20; Found: C, 67.07; H, 4.52; N, 11.31

EXAMPLE 10

To 4 ml of ethanolamine were added 760 mg of ethyl 5-hydroxy-8,11-dimethoxybenzo[a]phenazine-6-carboxylate, and the mixture was heated at 150° C. with stirring for 4 hours. The reaction mixture was cooled and poured into ice water. The precipitated solid was collected by filtration and recrystallized from dimethylformamide to give 727 mg (92.5% yield) of 5-hydroxy-N-β-hydroxyethyl-8,11-dimethoxybenzo[a]-phenazine-6-carboxyamide as yellow needles, m.p. 267°–269° C., Anal. Calcd. (%) for $C_{21}H_{19}N_3O_5$: C, 64.11; H, 4.87; N, 10.68; Found: C, 64.16; H, 4.63; N, 10.68

EXAMPLE 11

To a solution of 1000 mg of 5-hydroxy-N-β-hydroxyethylbenzo[a]phenazine-6-carboxyamide in 30 ml of dry chloroform was added 300 mg of triethylamine, followed by 660 mg of thionyl chloride. The mixture was heated at reflux for 30 minutes and evaporated to dryness under reduced pressure. The residue was dissolved in chloroform, washed with water, dried and the solvent was evaporated. The resulting residue was recrystallized from dimethylformamide to obtain 856 mg (91.8% yield) of 5-hydroxy-N-β-chloroethylbenzo[a]-phenazine-6-carboxyamide as yellow needles, m.p. 183°–186° C., Anal. Calcd. (%) for $C_{19}H_{14}N_3O_2Cl$: C, 64.87; H, 4.01; N, 11.94; Found: C, 64.60; H, 4.03; N, 11.66

EXAMPLE 12

To a suspension of 100 of 5-hydroxy-N-β-chloroethylbenzo[a]phenazine-6-carboxyamide in 10 ml of ethanol was added an excess amount of diazomethane ethereal solution, followed by stirring at room temperature overnight. The solvent was concentrated under reduced pressure, and the resulting solid was recrystallized from acetic acid to give 103 mg (99% yield) of 5-methoxy-N-β-chloroethylbenzo[a]-phenazine-6-carboxyamide as yellow needles, m.p. 211°–213° C., Anal. Calcd. (%) for $C_{20}H_{16}N_3O_2Cl$; C, 65.89; H, 4.29; N, 11.28; Found: C, 65.67; H, 4.41; N, 11.49

EXAMPLE 13

A mixture of 352 mg of 5-hydroxy-N-β-chloroethyl-benzo-[a]phenazine-6-carboxyamide, 0.5 ml of a 50% aqueous solution of dimethylamine and 5 ml of ethanol were heated at 100° C. for 2 hours in a sealed tube. The solvent was removed under reduced pressure and the resulting solid was recrystallized from dimethylformamide to afford 362 mg (90% yield) of 5-hydroxy-N-β-dimethylaminoethylbenzo[a]phenazine-6-carboxyamide as yellow amorphous powder, m.p. 176°–177° C., Anal. Calcd. (%) for $C_{21}H_{20}N_4O_2$: C, 69.98; H, 5.59; N, 15.55; Found: C, 70.26; H, 5.56; N, 15.73

EXAMPLE 14

A mixture of 352 mg of 5-hydroxy-N-βchloroethyl-benzo-[a]phenazine-6-carboxyamide, 0.5 ml of diethylamine and 0.1 g of sodium carbonate in 5 ml of ethanol was heated in a sealed tube on a steam bath.

The reaction mixture was filtered and the filtrate was concentrated. The resulting residue was recrystallized from methanol to afford 273 mg (70.4% yield) of 5-hydroxy-N-β-diethylaminoethylbenzo[a]phenazine-6-carboxyamide as orange prisms, m.p. 227°–231° C., Anal. Calcd. (%) for $C_{23}H_{24}N_4O_2$: C, 71.11; H, 6.23; N, 14.42; Found: C, 71.29; H, 6.35; N, 14.35

EXAMPLE 15

A mixture of 352 mg of 5-hydroxy-N-β-chloroethyl-benzo-[a]phenzine-6-carboxyamide and 120 mg of morpholine in 4 ml of dimethylformamide was heated at reflux for 2 hours.

The reaction mixture was cooled and the precipitated solid was collected by filtration and recrystallized from dimethylformamide to give 340 mg (84.6% yield) of 5-hydroxy-N- β-1-morpholinoethylbenzo[a]phenazine-6-carboxyamide as yellow needles, m.p. 166°–167° C., Anal. Calcd. (%) for $C_{23}H_{24}N_4O_3$: C, 68.64; H, 5.51; N, 13.92; Found: C, 68.58; H, 5.30; N, 13.68

EXAMPLE 16

A mixture of 378 mg of ethyl 5-hydroxy-8,11-dimethoxybenzo[a]phenazine-6-carboxylate and 120 mg of N,N-diethylethylenediamine in 50 ml of benzene was refluxed for 48 hours. The reaction mixture was filtered while hot. The filtrate was concentrated to a small volume and left to cool to obtain 367 mg (81.9% yield) of N-β-diethylaminoethyl-5-hydroxy-8,11-dimethoxybenzo[a]phenazine-6-carboxyamide as yellow needles, m.p. 210°–211.5° C., Anal. Calcd. (%) for $C_{25}H_{28}N_4O_4$: C, 66.94; H, 6.29; N, 12.49; Found: C, 66.72; H, 6.03; N, 12.60

EXAMPLE 17

Following a procedure similar to that of Example 16 using 378 mg of ethyl 5-hydroxy-8,11-dimethoxybenzo[a]-phenazine-6-carboxylate and 135 mg of N,N-diethylaminopropylenediamine, there were obtained 352 mg (76.2% yield) of N-γ-diethylaminopropyl-5-hydroxy-8,11-dimethoxybenzo[a]-phenazine-6-carboxyamide, m.p. 194°–196° C., Anal. Calcd. (%) for $C_{26}H_{30}N_4O_4$: C, 67.51; H, 6.54; N, 12.11; Found: C, 66.51; H, 6.26; N, 11.93

EXAMPLE 18

A mixture of 112 mg of 5-hydroxy-6-morpholinocarbonylbenzo[a]phenazine and 19 mg of sodium hydride in 25 ml of dry benzene was refluxed for 3 hours under a nitrogen atmosphere. The reaction mixture ws cooled, to which was then added dropwise a solution of 3-dimethylaminopropylchloride, freshly prepared from 1000 mg of 3-dimethylaminopropylchloride hydrochloride, in 15 ml of dry benzene, followed by heating at reflux overnight. Water was added and the benzene phase was separated. The aqueous layer was extracted twice with chloroform. The combined solution was dried and evaporated under reduced pressure. To the resulting residue was added a small amount of petroleum ether for crystallization to afford 94 mg (68.1% yield) of 5-γ-dimethylaminopropyloxy-6-morpholinocarbonyl-benzo[a]phenazine as orange powder, m.p. 115°–118° C., Anal. Calcd. (%) for $C_{26}H_{28}N_4O_3$: C, 70.25; H, 6.35; N, 12.60; Found: C, 69.98; H, 6.38; N, 12.80

What we claim is:

1. A compound of the formula

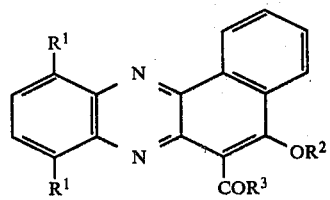

wherein $R^1$ is hydrogen of methoxy,
$R^2$ is hydrogen, methyl, acetyl, haloacetyl or aminoalkyl of the formula

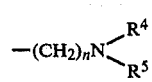

wherein $R^4$ and $R^5$ are alkyl having 2 or 3 carbon atoms, or $R^4$ and $R^5$ together with the nitrogen atom to which they are attached form morpholino or piperidino, and n is 2 or 3, and $R^3$ is ethoxy or amino of the formula

wherein $R^6$ is hydrogen and $R^7$ is alkyl which has 2 or 3 carbon atoms and is substituted with halogen, hydroxy, acetoxy, diemethylamino or diethylamin and $R^6$ or $R^7$ together with the nitrogen atom to which they are attached form morpholino.

2. A compound according to claim 1 wherein $R^1$ is hydrogen, $R^2$ is hydrogen and $R^3$ is N,N-dimethylaminoethylamino.

3. A compound according to claim 1 wherein $R^1$ is hydrogen, $R^2$ is hydrogen and $R^3$ is N,N-dimethylaminopropylamino.

4. A compound according to claim 1 wherein $R^1$ is methoxy, $R^2$ is hydrogen and $R^3$ is N,N-dimethylaminoethylamino.

5. A compound according to claim 1 wherein $R^1$ is methoxy, $R^2$ is hydrogen and $R^3$ is N,N-dimethylaminopropylamino.

* * * * *